United States Patent [19]

Bettin

[11] 4,262,567

[45] Apr. 21, 1981

[54] DEVICE FOR COOLING MICROTOME BLADE

[76] Inventor: Elizabeth M. Bettin, 228 S. Kensington Ave., LaGrange, Ill. 60525

[21] Appl. No.: 80,461

[22] Filed: Oct. 1, 1979

[51] Int. Cl.³ .......................... B26D 7/08; G01N 1/06
[52] U.S. Cl. .............................. 83/171; 62/DIG. 10; 83/915.5
[58] Field of Search ............... 83/915.5, 171, 16, 169, 83/15, 170; 62/320, DIG. 10

[56] References Cited

U.S. PATENT DOCUMENTS

| | | | |
|---|---|---|---|
| 2,643,579 | 6/1953 | Jacoby, Jr. ..................... | 83/915.5 X |
| 3,093,135 | 6/1963 | Hirschhorn ..................... | 128/303.1 |
| 3,203,290 | 8/1965 | Ashby ............................ | 83/171 |
| 3,220,290 | 11/1965 | Shandon ........................ | 83/915.5 X |
| 3,259,131 | 7/1966 | Kanbar et al. ................. | 128/303.1 |
| 3,296,821 | 1/1967 | Malinin .......................... | 83/915.5 X |
| 3,455,304 | 7/1969 | Gans .............................. | 128/303.1 |
| 3,456,538 | 7/1969 | Barton et al. .................. | 83/171 |
| 3,495,490 | 2/1970 | Dollhopf ........................ | 83/171 |
| 3,664,412 | 5/1972 | Zerkle ............................ | 62/DIG.10 X |
| 3,929,136 | 12/1975 | Kreeb et al. ................... | 128/303.1 |

OTHER PUBLICATIONS

Effective Use & Proper Care of the Microtome, Oscar W. Richards, copyright 1959, pp. 57-59, Published by American Optical Corp.
Manual of Histologic Staining Methods of the Armed Forces Institute of Pathology, Third Edition, McGraw-Hill Book Co., copyright 1968, p. 26.
Sectioning of Parafin Embedded Brain Tissues an Alternate Method, Bettin & Tamasevicius, Histo-Logic, vol. IX, No. 1, Jan., 1979, pp. 123, 124.

*Primary Examiner*—Frank T. Yost
*Attorney, Agent, or Firm*—Vogel, Dithmar, Stotland, Stratman & Levy

[57] ABSTRACT

A small container contains a frozen liquid or other coolant and is magnetically adhered to a metal microtome blade either by means of a permanent magnet disposed within the container or a magnetized metal wall portion on the container, for cooling the blade. The container may be sealed or refillable. There is also disclosed a container having inlet and outlet openings for permitting a continuous flow therethrough of coolant such as carbon dioxide from a dry ice source.

10 Claims, 9 Drawing Figures

DEVICE FOR COOLING MICROTOME BLADE

BACKGROUND OF THE INVENTION

The present invention relates to microtome blades and, in particular, means for cooling such blades.

A microtome is a specialized machine utilized for cutting very thin sections, typically 2-15 microns in thickness, of plant or animal tissue for use in histology. Typically, the tissue has been embedded in a firm matrix of paraffin, celloidin, carbowax or similar material in order to facilitate cutting and to preserve the structural composition of the tissue. The sections cut are put onto slides, stained with dyes specific for particular structures, and viewed under a light microscope.

The histologic method used for cutting paraffin-embedded tissues is to put the tissue block on ice for several minutes, then attach it to the microtome and cut sections with the microtome blade at room temperature. However, it has been a regular practice in the cutting of certain tissues to cool the microtome blade in lieu of or in addition to cooling of the tissue block.

Several techniques have been used to effect cooling of the microtome blade. The simplest is holding an ice cube against the blade until it is cooled and then repeating this process as the temperature of the blade rises. This is, however, a very messy and inconvenient method because of the water from the melting ice cube.

Attempts have also been made to design various pieces of equipment to continuously cool the microtome blade. Such equipment is disclosed, for example, in "Effective Use And Proper Care of the Microtome", by Oscar W. Richards, Copyright 1959, pages 57–59. Such arrangements have, however, been short-lived and unsuccessful due to their excessive costs and to the intricacies of their design, frequently involving tanks of carbon dioxide, tubing, small motors and sometimes special knife blades designed for use only with that cooling equipment. Such prior art arrangements frequently limited the freedom of movment of the technician and thus had questionable merit.

SUMMARY OF THE INVENTION

The present invention relates to a device for cooling cutting blades such as microtome blades, which device avoids the disadvantages of prior art techniques and affords additional structural and operational advantages.

It is a general object of this invention to provide a device for cooling a microtome blade, which device is substantially neat and dry and minimizes the risk of dripping water on the microtome blade or other parts of the microtome.

It is another object of this invention to provide a device of the type set forth, which is of simple and economical construction and requires no special equipment other than a common refrigerator-freezer which is available in virtually all histology laboratories.

Still another object of this invention is to provide a cooling device of the type set forth which can be easily detachably mounted on the microtome blade.

These and other objects of the invention are attained by providing a device for cooling a cutting blade comprising a container, a coolant disposed in the container, and mounting means for removably attaching the container to the cutting blade.

Further features of the invention pertain to the particular arrangement of the parts of the cooling device whereby the above-outlined and additional operating features thereof are attained.

The invention, both as to its organization and method of operation, together with further objects and advantages thereof, will best be understood by reference to the following specification taken in conjunction with the accompanying drawings:

DESCRIPTION OF THE PREFERRED EMBODIMENTS

Figure 1:
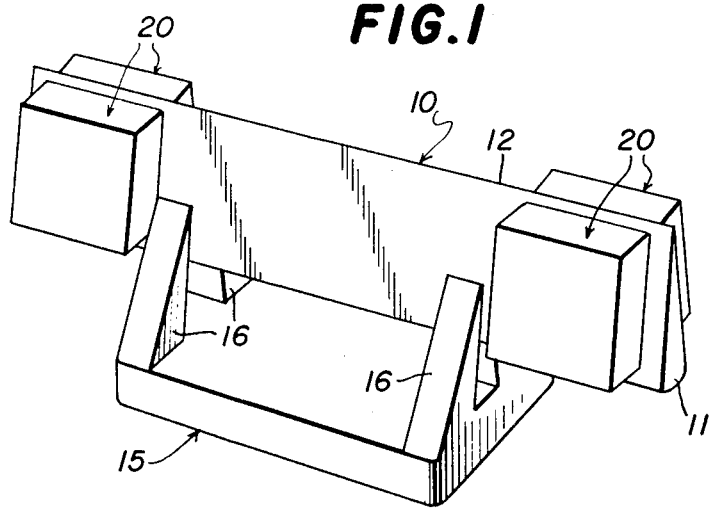
FIG. 1 is a perspective view of a microtome blade and holder therefor, with several cooling blocks constructed in accordance with the present invention attached to the blade.

Referring to FIG. 1 of the drawings, there is illustrated a microtome blade, generally designated by the numeral 10, having an enlarged or relatively thick base 11 and a knife edge 12. The blade 10 is preferably formed of steel or other suitable metal and is fixedly secured in a holder, generally designated by the numeral 15, which forms a part of a mircotome (not shown). More specifically, the holder has a plurality of arms 16 for grippingly engaging the base 11 of the microtome blade 10 securely to hold it in place. It will be appreciated that the holder 15 has been illustrated in diagrammatic form, since it forms no part of the present invention, but in actual practice the holder will be somewhat more complicated in construction and will typically include means for adjustably positioning and gripping the microtome blade 10.

Figure 3:
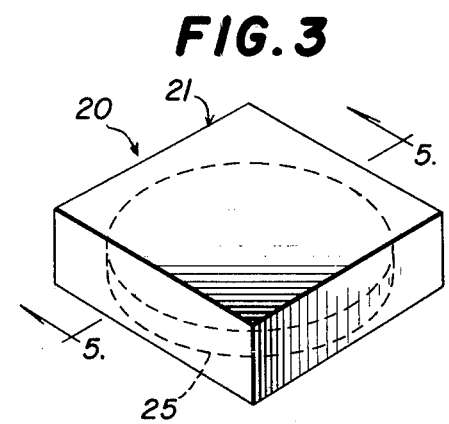
FIG. 3 is a perspective view of a cooling block constructed in accordance with and embodying the features of a first embodiment of the present invention.
Figure 5:
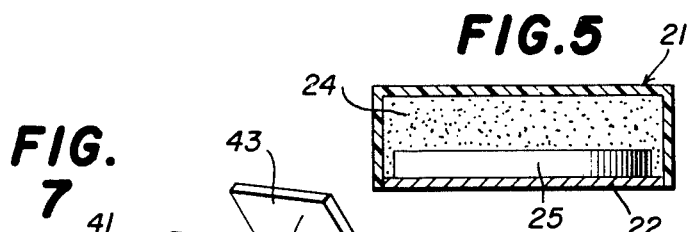
FIG. 5 is a view in vertical section taken along the line 5—5 in FIG. 3.

Referring to FIGS. 3 and 5 of the drawings, there is illustrated a first embodiment of a cooling block, generally designated by the numeral 20, constructed in accordance with and embodying the features of the present invention. The cooling block 20 includes a container 21, generally in the shape of a hexahedron, which may be formed of metal, plastic, or any other suitable material. At least one wall 22 of the container 21 is preferably formed of a good thermally conducting material, this wall 22 being flat and adapted to be disposed against the side of the microtome blade 10, as will be described more fully below. The cooling block 20 is permanently sealed or closed in watertight condition and contains therein a coolant 24 which is preferably a freezable liquid such as water. If lower temperatures are desired, it will be appreciated that the coolant 24 could be a material having a freezing point substantially lower than that of water, such as ethylene glycol or the like. Also disposed within the container 21 is a permanent magnet 25.

In use, the container 21 is placed in a freezer, preferably oriented so that the magnet 25 lies against the wall 22. When the coolant 24 is frozen, the cooling block 20 is ready for use in cooling the microtome blade 10. For this purpose, the wall 22 is placed against the side of the microtome blade 10, as illustrated in FIG. 1, the magnet 25 serving to hold the cooling block 20 in contact with the metal microtome blade 10. If desired, a plurality of the cooling blocks 20 may be attached to the microtome blade 10, as illustrated in FIG. 1, on one or both sides of the blade and at different locations therealong outside the holder arms 16.

Figure 2:
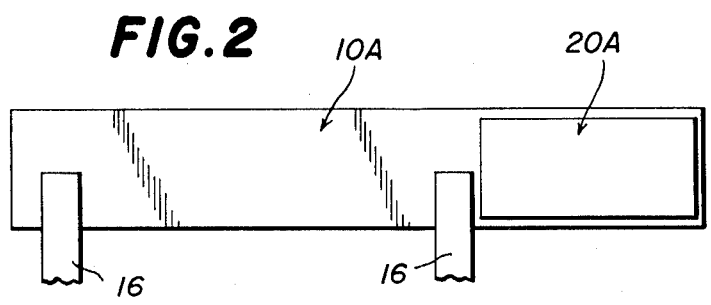
FIG. 2 is a fragmentary side elevational view of a microtome blade in a different mounting arrangement and with a different shape cooling block thereon.

It will be appreciated that the container 21 is dimensioned to fit on the microtome blade 10 and, typically, may be 1 inch in height, 1 inch in length and have a depth of ¼ to ½ inch. It will, however, be appreciated that the cooling block 20 could be made in any desired size and shape, depending upon the size and mounting configuration of the microtome blade 10. Thus, referring to FIG. 2, there is illustrated a slightly different mounting arrangement of a microtome blade 10A, wherein one end of the microtome blade 10A is disposed very close to the adjacent pair of holder arms 16. For this purpose a slightly enlarged and elongated cooling block 20A could be used for mounting on the overhanging opposite end of the microtome blade 10A.

Figure 4:
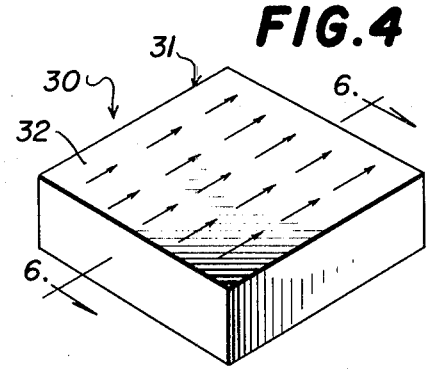
FIG. 4 is a perspective view similar to FIG. 3, of a cooling block constructed in accordance with and embodying the features of a second embodiment of the present invention.
Figure 6:
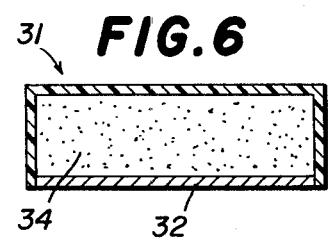
FIG. 6 is a view in vertical section taken along the line 6—6 in FIG. 4.

Referring to FIGS. 4 and 6 of the drawings, there is illustrated another embodiment of the cooling block of the present invention, generally designated by the numeral 30. The cooling block 30 includes a container 31, which may be the same shape as the container 21, and may be formed of any suitable material. The container 31, however, includes a flat wall 32 which is formed of a magnetized metal. The container 31 is preferably permanently closed or sealed and contains therein a suitable coolant 34.

The cooling block 30 operates in substantially the same manner as the cooling block 20 except that attachment to the microtome blade 10 is afforded by the magnetized metal wall 32 of the container 31, rather than by a permanent magnet contained within the container 31.

Figure 7:
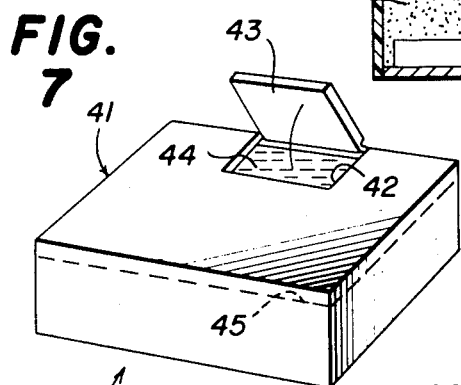
FIG. 7 is a perspective view of a cooling block constructed in accordance with and embodying the features of a third embodiment of the present invention.

In FIG. 7 there is illustrated still another embodiment of the cooling block of the present invention, generally designated by the numeral 40, which includes a container 41 which may be the same in construction, size and shape as either one of the containers 21 or 31. The cooling clock 40, however, differs in that it is refillable, being provided with an access opening 42 therein closable by a hinged flap 43 formed in one wall of the container 41. The flap 43 may be provided with a snap-type watertight closure.

In use, a coolant 44 is inserted into the container through the opening 42 and is filled to a level 45. If the coolant 44 is water or other material which expands when frozen, the level 45 is slightly below the top of the container to allow room for expansion. The flap 43 is then closed and the cooling block 40 is placed in a freezer until the coolant 44 is frozen and is then used in exactly the same manner as was described above in connection with the cooling blocks 20 or 30. Preferably, the attachment wall of the cooling block 40 will be on the side thereof opposite the flap 43.

Figure 8:
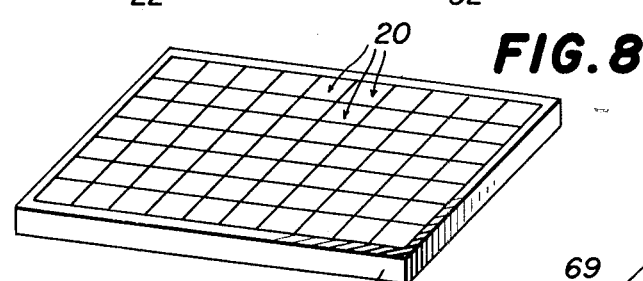
FIG. 8 is a reduced perspective view of a freezing tray for containing a plurality of cooling blocks of the present invention for freezing thereof.

Referring now to FIG. 8 of the drawings, there is illustrated a tray 50 for containing a plurality of the cooling blocks 20, 30 or 40. The tray 50 may be used for simultaneously freezing a large number of cooling blocks. This is desirable since a number of the cooling blocks 20, 30 or 40 may have to be used in a given period of time because, as the coolant thaws and begins to warm up, the cooling block must be replaced with a fresh one to maintain the temperature of the microtome blade 10 at the desired level. Thus, as the coolant of each cooling block melts, it is replaced in a tray 50 and a fresh block is removed from a frozen tray. When a tray of thawed cooling blocks is filled, it is then reinserted into the freezer for freezing.

Figure 9:
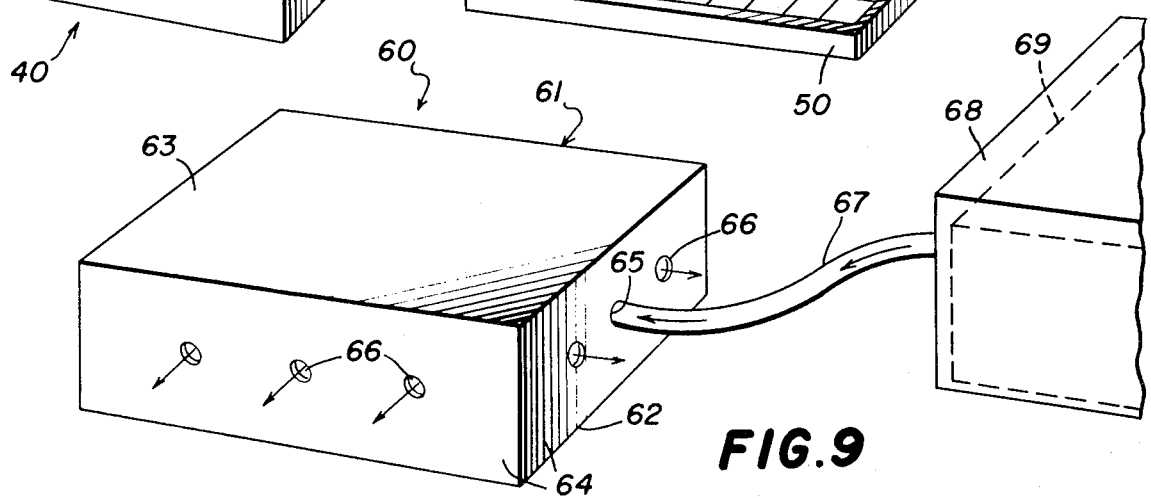
FIG. 9 is an enlarged fragmentary perspective view of a cooling block constructed in accordance with and embodying the features of a fourth embodiment of the present invention, illustrated coupled to an associated source of coolant.

Referring to FIG. 9, there is illustrated still another embodiment of cooling block, generally designated by the numeral 60, which includes a container 61, which may be of the same general size and shape as the containers 21, 31 and 41, having parallel rear and front walls 62 and 63 interconnected by peripheral side walls 64. Formed in one of the side walls 64 is an inlet aperture 65. Also formed in the side walls 64 at spaced-apart points therealong is a plurality of outlet apertures 66. Connected to the inlet aperture 65 is one end of a conduit 67, the other end of which is connected to a reservoir 68 or other source of coolant such as dry ice 69.

In use, the container 61 is attached to the microtome blade 10 in the same manner as was described above in connection with either of the cooling blocks 20 or 30. Preferably, the microtome blade 10 is disposed below the reservoir 68 of coolant so that the carbon dioxide may flow by gravity through the conduit 67 into the container 61 and then exit the container 61 through the outlet apertures 66. In this way, there is provided a continuous cooling of the microtome blade 10.

It will be appreciated that the cooling blocks of the present invention can be used to cool other types of cutting blades. It will also be appreciated that any suitable type of coolant could be utilized, but most typically water will be used because it is readily accessible in all histological laboratories. It will also be understood that, depending upon the nature of the coolant, it might not actually freeze in a typical refrigerator freezing unit such as is normally available in histological laboratories.

From the foregoing, it can be seen that there has been provided an improved device for cooling microtome blades, which is of simple and economical construction and characterized by ease and simplicity of use.

While there have been described what are at present considered to be preferred embodiments of the invention, it will be understood that various modifications may be made therein, and it is intended to cover in the appended claims all such modifications as fall within the true spirit and scope of the invention.

What is claimed is:

1. In a microtome including a cutting blade and a support therefor, self-contained blade cooling apparatus comprising a closed container, a coolant confined within said container, and mounting means for removably attaching said container to the cutting blade in thermal contact therewith independently of the blade support.

2. The device of claim 1, wherein said container has a sealable opening therein for filling and emptying thereof.

3. The device of claim 1, wherein said coolant is water.

4. The device of claim 1, wherein said coolant is a liquid having a freezing point substantially lower than the freezing point of water.

5. The device of claim 1, wherein said coolant is a freezable liquid.

6. The device of claim 1, wherein the cutting blade is formed of ferrous metal, said mounting means being magnetic.

7. The device of claim 6, wherein said mounting means comprises a permenent magnet disposed inside said container.

8. The device of claim 1, wherein said mounting means comprises a magnetized metal wall portion on said container adapted to be disposed against the cutting blade.

9. The device of claim 1, wherein said container includes a thermally conductive wall portion adapted to be disposed in engagement with the cutting blade.

10. The device of claim 1, wherein said coolant is dry ice.

* * * * *